US009033575B2

(12) United States Patent  
Martinez Ferreira

(10) Patent No.: US 9,033,575 B2  
(45) Date of Patent: May 19, 2015

(54) ARC-SHAPED MEDICAL IMAGING EQUIPMENT

(75) Inventor: Carlos Martinez Ferreira, Buc (FR)

(73) Assignee: GENERAL ELECTRIC COMPANY, Schenectady, NY (US)

(*) Notice: Subject to any disclaimer, the term of this patent is extended or adjusted under 35 U.S.C. 154(b) by 256 days.

(21) Appl. No.: 13/426,646

(22) Filed: Mar. 22, 2012

(65) Prior Publication Data

US 2012/0243659 A1    Sep. 27, 2012

(30) Foreign Application Priority Data

Mar. 25, 2011   (EP) .................................. 11305337

(51) Int. Cl.
  *H05G 1/02*   (2006.01)
  *A61B 6/00*   (2006.01)

(52) U.S. Cl.
  CPC .............. *A61B 6/587* (2013.01); *A61B 6/4441* (2013.01)

(58) Field of Classification Search
  CPC .................................................... A61B 6/4441
  USPC .......................................... 378/196, 197, 198
  See application file for complete search history.

(56) References Cited

U.S. PATENT DOCUMENTS

| | | | | |
|---|---|---|---|---|
| 3,549,885 A | * | 12/1970 | Andersson | 378/197 |
| 4,987,585 A | * | 1/1991 | Kidd et al. | 378/197 |
| 2001/0005410 A1 | * | 6/2001 | Rasche et al. | 378/197 |
| 2004/0066880 A1 | * | 4/2004 | Oikawa | 378/4 |

FOREIGN PATENT DOCUMENTS

EP            1493388 A1    1/2005

OTHER PUBLICATIONS

Search Report and Written Opinion from corresponding EP application No. 11305337.5, dated Aug. 1, 2011.

* cited by examiner

*Primary Examiner* — Glen Kao  
(74) *Attorney, Agent, or Firm* — GE Global Patent Operation; Marc A. Vivenzio

(57) ABSTRACT

Medical imaging equipment is provided. The medical imaging equipment comprises a support assembly, an arc-shaped member slidably mounted on the support assembly, a radiation source mounted on the arc-shaped member in the vicinity of a first distal end of the arc-shaped member and being oriented to radiate along the direction of an imaging axis, and a detector mounted on the arc-shaped member in the vicinity of the second distal end of the arc-shaped member and being oriented to face the source along the imaging axis, wherein the radiation source and the detector are respectively mounted on one side and the other of the mid plane of the arc-shaped member.

7 Claims, 5 Drawing Sheets

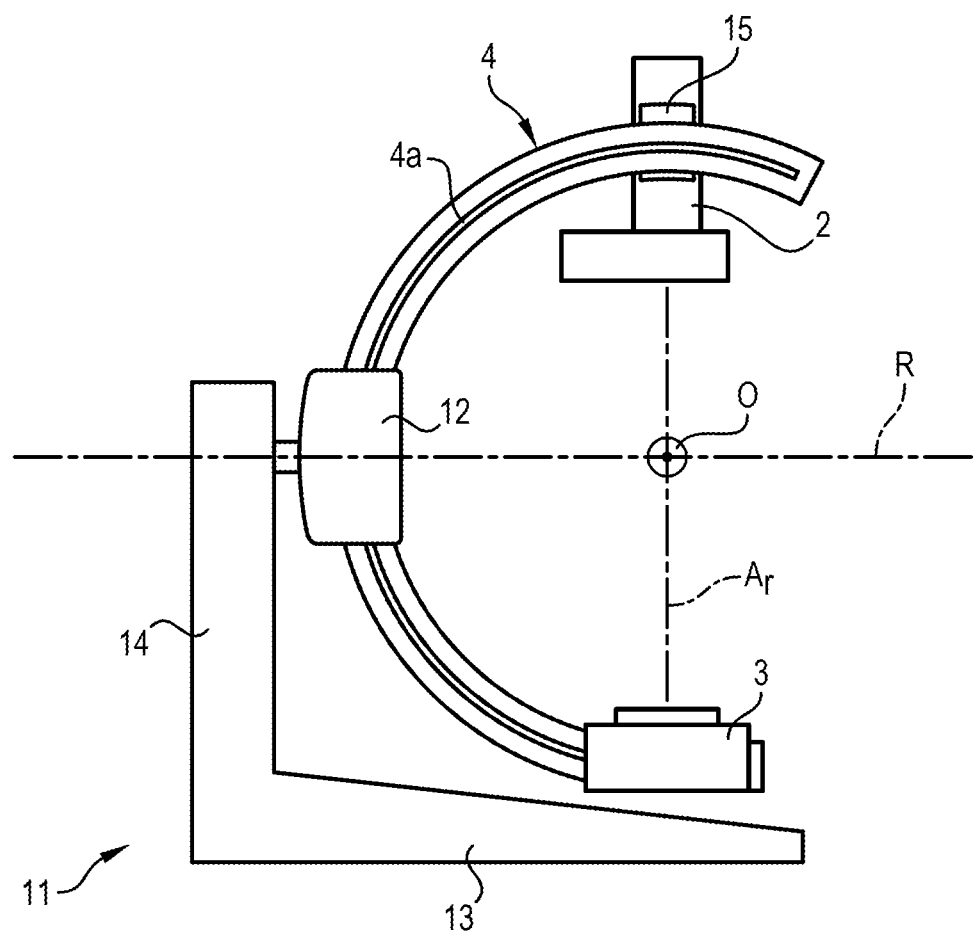

ARC-SHAPED MEDICAL IMAGING EQUIPMENT

BACKGROUND OF THE INVENTION

1. Field of the Invention

Embodiments of the invention relate to medical imaging systems and, more particularly, to C-arm equipment.

2. Description of Related Art

C-arm medical imaging systems usually comprise an X-ray source and an X-ray detector, wherein the X-ray source and the X-ray detector are mounted on opposing ends of the C-arm gantry so that X-rays emitted by the source are incident on and detectable by the X-ray detector. The source and the detector are positioned so that, when an object (e.g., a human extremity) is interposed therebetween and is irradiated with X-rays, the detector produces data representative of characteristics of the interposed object. The data produced is displayed on a monitor or electronically stored.

C-arm equipment is used for surgical planning, co-registration, image fusion, navigation, implant fitting, surgical validation, etc. During these procedures, it is desirable to observe the patient from several different orientations and to do so without the need to reposition the patient. C-arm equipment has developed to meet these needs and is well known in the medical and surgical arts.

The C-arm is slidably mounted on a support assembly and defines an axis of rotation (perpendicular to the plane of the C-arm) about which the source and the detector are rotatable. By positioning this axis of rotation at or near an object, and by rotating the source and detector around the object in an orbital motion in the plane of the C-arm, images of the object taken at a plurality of different orientations can be obtained. These images can be combined to generate a comprehensive three-dimensional image of the object. The process of combining images to produce a comprehensive three-dimensional image is commonly performed with reconstructive software.

The C-arm is also typically rotatable on the support assembly, around a longitudinal axis parallel to the plane of the C-arm. By being rotatable about at least two different axes, the C-arm may be positioned at many different orientations in order to take images from different desirable perspectives. Thus, the mobile C-arm imaging machine greatly increases the efficiency and ease of taking images of a patient before and during a medical procedure.

C-arm imaging machines, such as those commercialized by GE Medical Systems (Innova®), can comprise a C-arm with a rotational axis offset relatively to the plane of the C-arm. The source and the detector are adjacent to the distal ends of the C-arm and are also offset from the plane of the C-arm, so that the axis of rotation of the orbital motion, as well as the longitudinal rotational axis of the C-arm, and the image axis intersect on a common point.

Such machines have the advantage of avoiding the complexity of other C-arm machines and of providing a large gap between the source and the detector. However, due to the offset, they present a large gantry volume and the range of movement of the C-arm around the longitudinal offset is limited.

Other C-arm imaging systems have a source and a detector, wherein the axis of the source and the detector extends in the median plane of the C-arm. Although this configuration authorizes smaller gantry volumes and a higher range of movement for the C-arm, the gap between the source and the detector is limited due to the height of the tube extending within the internal space of the C-arm.

Other C-arm equipment also use double slide rails to increase the imaging capacity of the machine. However, this equipment is of high complexity and gantry volume.

In view of the foregoing, there exists a need for C-arm imaging equipment that is of small volume, for use in operating or exam situations, and that provides a large gap between the source and detector, without being of complex structure, to allow the device to easily access a patient while enabling a wide range of movement and positions.

BRIEF DESCRIPTION OF THE INVENTION

According to an embodiment of the present invention, medical equipment is provided. The medical imaging equipment comprises a support assembly, an arc-shaped member slidably mounted on the support assembly, a radiation source mounted on the arc-shaped member in the vicinity of a first distal end of the arc-shaped member and being oriented to radiate along the direction of an imaging axis, and a detector mounted on the arc-shaped member in the vicinity of the second distal end of the arc-shaped member and being oriented to face the source along the imaging axis and is mounted, wherein the radiation source and the detector are respectively mounted on one side and the other of the mid plane of the arc-shaped member. According to another embodiment of the present invention, a medical imaging system comprising medical imaging equipment is provided. The medical imaging equipment comprises a support assembly, an arc-shaped member slidably mounted on the support assembly, a radiation source mounted on the arc-shaped member in the vicinity of a first distal end of the arc-shaped member and being oriented to radiate along the direction of an imaging axis, and a detector mounted on the arc-shaped member in the vicinity of the second distal end of the arc-shaped member and being oriented to face the source along the imaging axis and is mounted, wherein the radiation source and the detector are respectively mounted on one side and the other of the mid plane of the arc-shaped member. The medical imaging system further comprises a processing system comprising a calculation unit configured to process images to generate a comprehensive three-dimensional image.

BRIEF DESCRIPTION OF THE DRAWINGS

Other objects, features and advantages of the embodiments of the present invention will appear on reading the following description, given only as a non-limiting example, and made with reference to the appended drawings in which:

FIG. 4 is a side view of the C-arm equipment of FIG. 2; and

DETAILED DESCRIPTION OF THE INVENTION

Figure 1:
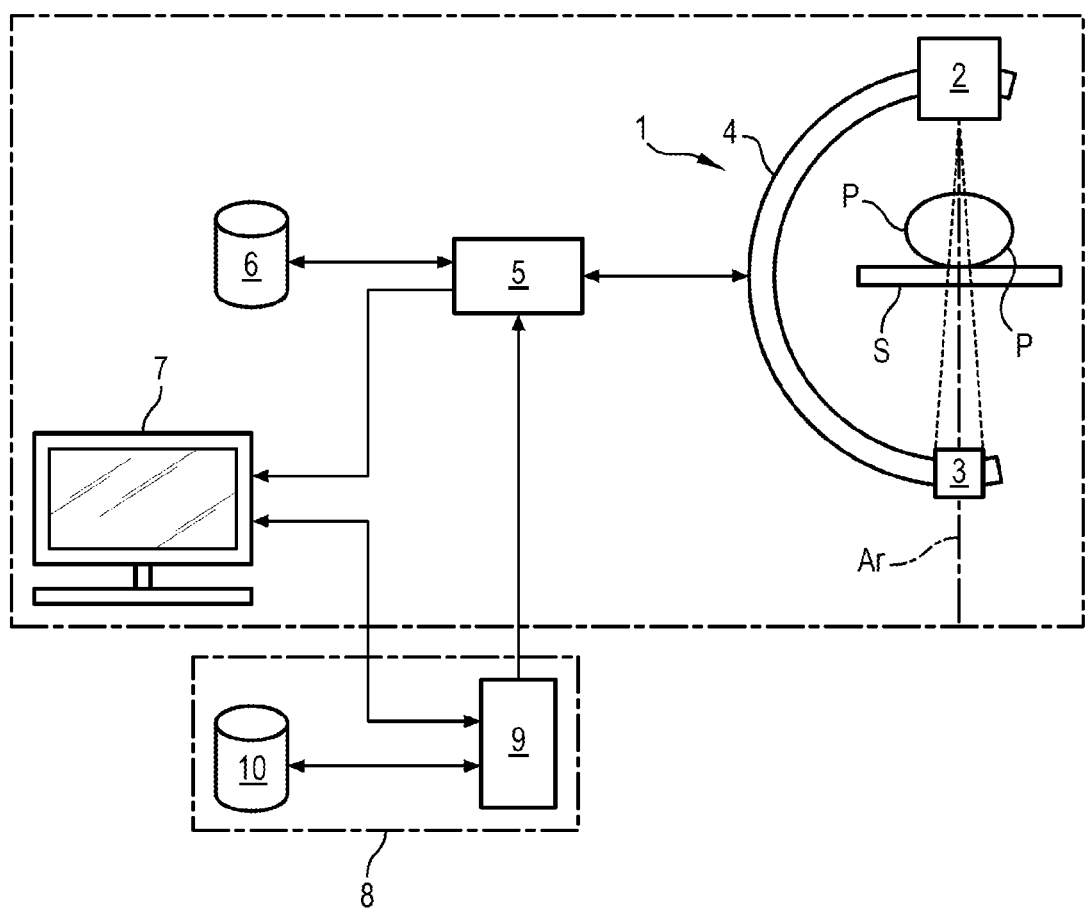
FIG. 1 is a schematic view of a medical imaging system according to an embodiment of the invention.

FIG. 1 illustrates a medical imaging system. The medical imaging system comprises C-arm equipment 1 with a source 2 and a detector 3 supported by an arc-shaped member 4 (also commonly known as a C-arm or C-arc). Equipment 1 also comprises a support S for receiving a patient P to be examined, a control unit 5, a storage unit 6 and a display unit 7.

The source 2 and the detector 3 are mounted on opposite ends of the arc-shaped-member 4. The source 2 may comprise an X-ray source and emits a radiation beam B along the direction of an imaging axis Ar through the zone of the patient to be examined The detector 3 detects the radiation emitted by the source 2. The detector may comprise a CCD sensor or a direct digital detector which directly converts the X-rays into digital signals.

The control unit 5 is linked to the C-arm equipment 1 and controls acquisition by fixing several parameters such as the radiation dose to be emitted and the positions and movements of the C-arm 4. The storage unit 6 records the acquired parameters and images. Such storage unit 6 is connected to the control unit 5 and can be located inside or outside of the control unit 5. The display unit 7 can be a display device of any known type. It is connected to the control unit 5 and allows a practitioner to control acquisition of radiological images.

Control unit 5, storage unit 6 and display unit 7 are also coupled to a processing system 8, which comprises a calculation unit 9 and storage unit 10. The processing system 8 receives images acquired and stored in the storage unit 6 and processes the images to generate, in particular, a comprehensive three-dimensional image.

Figure 2:
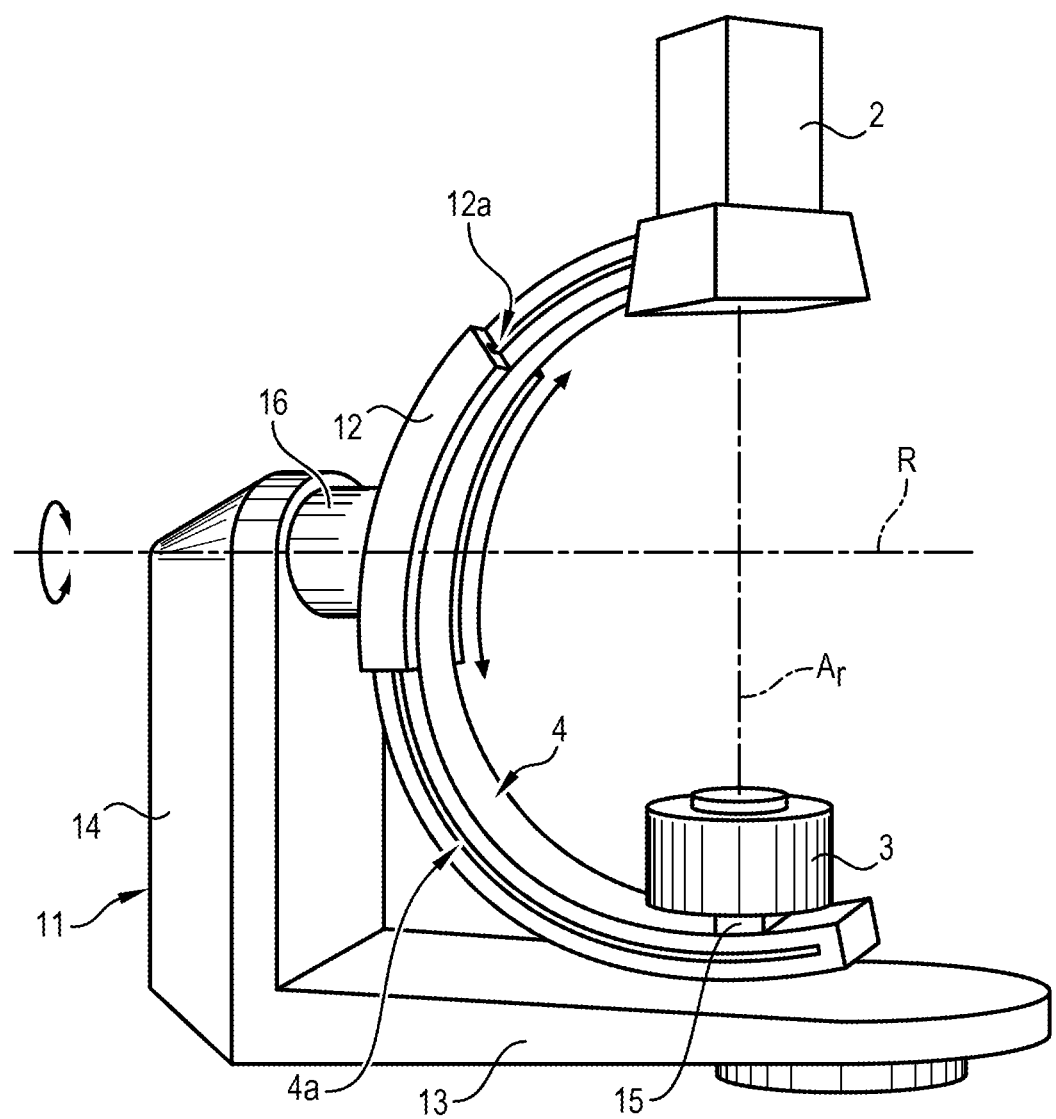
FIG. 2 is a perspective view of the C-arm equipment according to an embodiment of the invention.
Figure 3:
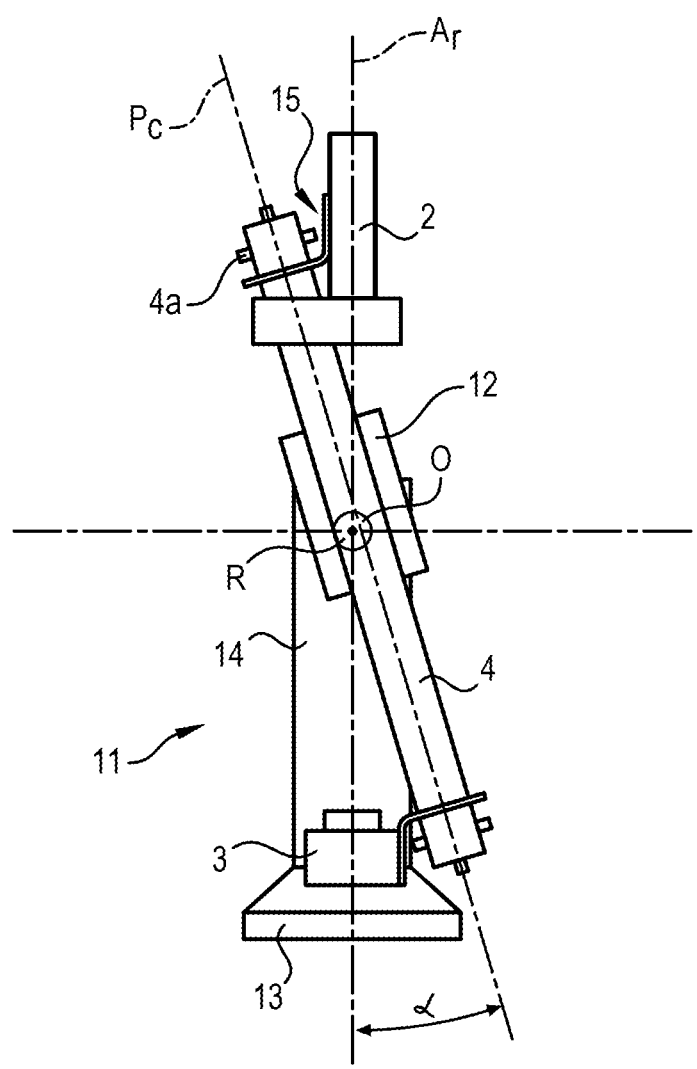
FIG. 3 is a front view of the C-arm equipment of FIG. 2.

FIGS. 2 through 4 illustrate, more particularly, the C-arm equipment 1, wherein the C-arm equipment 1 comprises a support assembly 11 and a curved guide 12 which is mounted on the support assembly 11. The curved guide 12 slidably carries the C-arm 4, so that the C-arm 4 can slide within the curve guide 12, thereby providing the orbital rotation movement of the source 2 and detector 4.

The figures illustrate that the C-arm equipment may be supported on the ground. The support assembly 11, in one embodiment, is L-shaped and includes a base 13 and a riser 14. The base 13 is adjacent to the floor, and can comprise wheels in order to be movable with respect to the floor. The riser 14 extends upward and is affixed to the arm base 13. Other forms of the support assembly 11 can be contemplated, in particular in the case of C-arm equipment that is mounted on the ceiling by a support carrier.

For example, the curved guide 12 may be a U-shaped rail. Each of the lateral walls of the curved guide 12 can comprise at least one groove 12a extending along the length of the curved guide 12 so that the curved guide 12 cooperates with corresponding projections 4a extending along the sides of the C-arm 4.

The curved guide 12 is pivotally mounted on riser 14 through a rotating support arm 16 which allows the curved guide 12 and C-arm 4 to rotate about a rotational axis R. The rotational axis R extends in the mid plane Pc (FIG. 3) of the L-shaped support assembly 11. The rotational axis R is parallel to the main direction of the base 13 and perpendicular to the riser 14, wherein the base 13 is horizontal.

The source 2 and the detector 3 are respectively on one side and the other of the mid plane Pc of the C-arm 4. The imaging axis Ar defined by the source 2 and detector 3 is thus inclined relative to the mid plane Pc of the C-arm 4. The mid plane Pc and the imaging axis Ar are angularly offset (angle α) and cross at a crossing point O between the rotational axis R and the imaging axis Ar. The source 2 being in the vicinity of a first distal end of the C-arm 4, wherein at least part of the source 2 extends laterally on one side of the C-arm 4, along the width of the C-arm 4. Part of the source 2 can also extend above the C-arm 4. The detector 3 faces the source 2 and extends laterally on the other side of the C-arm 4, in the vicinity of the opposite distal end of the C-arm 4.

In another embodiment of the invention, the control unit 5 is programmed to command various internal motors (not represented), which control the rotational movement of the arc-shaped member 4 around the rotational axis R, as well as the sliding movement of the member 4 within the curve guide 12, in order to move the source 2 and the detector 3 as follows.

In particular, the C-arm 4 can be inclined by rotation around the rotational axis R so as to permit acquisition in any detection plane. Once the source 2 and the detector 3 are positioned so that the plane defined by the imaging axis and the rotational axis R coincides with the desired detection plane and an orbital movement of the source 2 and the detector 3 in such detection plane can be controlled by the control unit 5. The orbital movement can be achieved through controlling, at the same time, a sliding movement of C-arm 4 within the curved guide 12 and a modification of the inclination of the C-arm 4 around rotational axis R, so as to maintain the plane defined by the imaging axis and the rotational axis R within the selected detection plane.

For example, when the detection plane is vertical, the C-arm 4 is angularly inclined, relative to a vertical angle, which is maximum when the imaging axis of the source 2 and the detector 3 is vertical and decreases as the imaging axis is toggled towards rotational axis R.

Figure 5A:
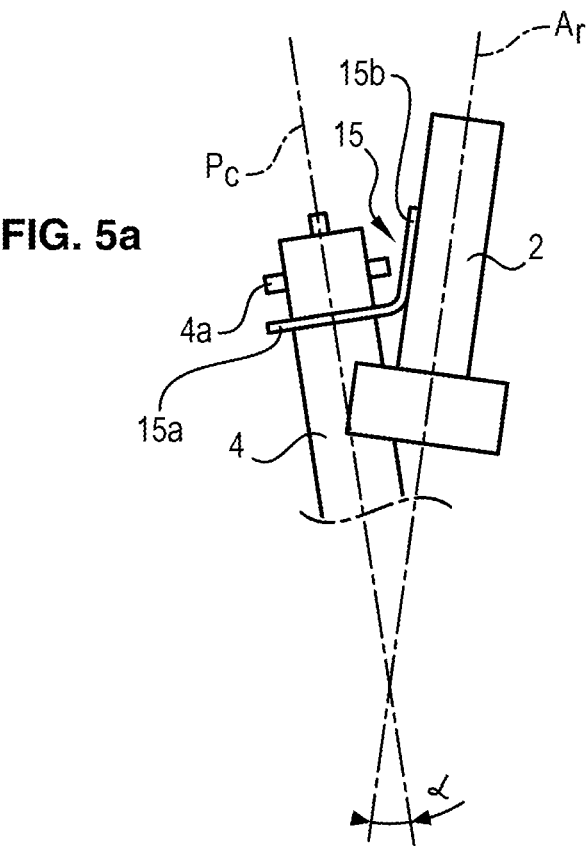
FIGS. 5a and 5b are detail views of the source and the detector mountings at the distal ends of the C-arm equipment of FIG. 2.
Figure 5B:
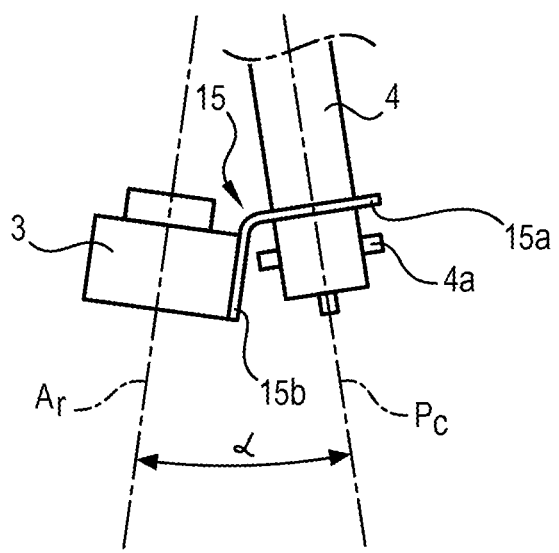

FIGS. 5a and 5b illustrate, in one embodiment of the invention, the source 2 and the detector 3 supported on the C-arm 4 through mounting plates 15 configured in an L-shape, wherein the mounting plates comprise a first branch 15a, which is internally fixed to the C-arm 4, and a second branch 15b, which is externally fixed on the source 2 or the detector 3. The two branches 15a, 15b of such mounting plate are bent relatively to each other so as achieve the angular offset (angle α) between the C-arc mid plane Pc and the imaging axis of the source 2 and the detector 3.

Furthermore, the C-arm 4 is fixed on the first branch 15a and dimensioned so that a gap is left between the C-arm 4 and the second branch 15b which bears the source 2 or the detector 3. The gap is greater than the thickness of the lateral walls of the curved guide 12 so that the sliding movement of the C-arm 4 along the curved guide 12 is not blocked by the mounting plates 15, the source 2 or the detector 3 when the source 2 or the detector 3 reach the zone of the curved guide 12. The C-arm 4 is on the side of the curved guide 12 and can continue to slide with the source 2 and the detector 3, thus sliding with a large range of movement.

What is claimed is:

1. Medical imaging equipment comprising:
    a support assembly;
    a curved guide mounted on the support assembly;
    an arc-shaped member slidably mounted on the curved guide, a curve of the arc-shaped member defining a mid plane (Pc) of the arc-shaped member, the arc-shaped member having first and second opposed ends;
    an X-ray radiation source mounted on the arc-shaped member in the vicinity of the first end and being oriented to radiate along the direction of an imaging axis; and
    a detector mounted on the arc-shaped member in the vicinity of the second and being oriented to face the source along the imaging axis,
    wherein the X-ray radiation source and the detector are respectively mounted on one side and the other of the mid plane (Pc) of the arc-shaped member, the curved guide carrying the arc-shaped member allowing orbital rotation movement of the source and detector.

2. The medical imaging equipment of claim 1, wherein the arc-shaped member is mounted rotatable about a rotational axis on the support assembly, and wherein the mid plane (Pc)

of the arc shaped member and the imaging axis are angularly offset and intersect at a crossing point between the rotational axis and the imaging axis.

3. The medical imaging equipment of claim 1, wherein at least part of the source extends laterally on one side of the mid plane Pc of the arc-shaped member, along a width of the arc-shaped member.

4. The medical imaging equipment of claim 3, wherein the detector extends laterally on the other side of the mid plane (Pc) of the arc-shaped member.

5. The medical imaging equipment of claim 1, wherein the arc-shaped member is mounted rotatable about a rotational axis on the support assembly, the equipment further comprising a control unit configured to simultaneously control a sliding movement of the arc-shaped member and the inclination of the arc-shaped member around the rotational axis so as to maintain the plane defined by the imaging axis and the rotational axis within a selected detection plane.

6. The medical imaging equipment of claim 1, wherein at least one of the source and the detector is supported on the arc shaped member through an L-shaped mounting plate.

7. The medical imaging equipment of claim 6, wherein the L-shaped mounting plate comprises two branches relative to each other at an angle corresponding to the angular offset between the arc shaped member and the imaging axis.

* * * * *